United States Patent
Zhang et al.

[11] Patent Number: 6,120,480
[45] Date of Patent: Sep. 19, 2000

[54] CATHETER INTRODUCER

[75] Inventors: John Zhang, Woburn; James Culhane, Westboro; Tai Kien, Lowell; Jon Norstrom, Winchendon; Michael LeBlanc, Bolton, all of Mass.

[73] Assignee: Medtronic AVE, Inc., Santa Rose, Calif.

[21] Appl. No.: 08/959,501

[22] Filed: Oct. 28, 1997

[51] Int. Cl.[7] .................................................. A61M 5/178
[52] U.S. Cl. ........................................ 604/164; 604/256
[58] Field of Search ................................. 604/164, 165, 604/166, 256, 264, 280, 523, 533, 535

[56] References Cited

U.S. PATENT DOCUMENTS

| | | |
|---|---|---|
| Re. 31,855 | 3/1985 | Osborne . |
| 1,147,408 | 7/1915 | Kells . |
| 3,030,953 | 4/1962 | Koehn . |
| 3,082,769 | 3/1963 | Palmer . |
| 3,308,819 | 3/1967 | Arp . |
| 3,388,703 | 6/1968 | Bowes . |
| 3,459,184 | 8/1969 | Ring . |
| 3,502,069 | 3/1970 | Silverman . |
| 3,612,050 | 10/1971 | Sheridan . |
| 4,027,668 | 6/1977 | Dunn . |
| 4,202,332 | 5/1980 | Tersteegen et al. . |
| 4,430,081 | 2/1984 | Timmermans . |
| 4,502,482 | 3/1985 | DeLuccia . |
| 4,629,450 | 12/1986 | Suzuki et al. . |
| 4,650,472 | 3/1987 | Bates . |
| 4,668,221 | 5/1987 | Luther . |
| 4,668,226 | 5/1987 | Omata et al. . |
| 4,698,056 | 10/1987 | Ciannella . |
| 4,772,266 | 9/1988 | Groshong . |
| 4,841,976 | 6/1989 | Packard et al. . |
| 4,862,891 | 9/1989 | Smith . |
| 4,895,564 | 1/1990 | Farrell . |
| 4,898,591 | 2/1990 | Jang et al. . |
| 4,899,787 | 2/1990 | Ouchi et al. . |
| 4,909,798 | 3/1990 | Fleishhacker et al. . |
| 4,961,731 | 10/1990 | Bodicky et al. . |

(List continued on next page.)

FOREIGN PATENT DOCUMENTS

| | | |
|---|---|---|
| 0738520 | 10/1996 | European Pat. Off. . |
| 7246241 | 9/1995 | Japan . |
| 7255857 | 10/1995 | Japan . |

OTHER PUBLICATIONS

Butto et al., "Modified Sheath Introducer for Reduced Arterial Damage", Radiology, 1987, 163:824–826.

Desilets, et al. "A New Method of Percutaneous Catheterization", American Journal of Roentgenology, Radium Therapy and Nuclear Medicine, vol. 97, No. 2, pp. 519–522.

Cordis Avanti® Sheath Introducers brochure, Jan. 1996.

Daig Fast–Cath™ Introducers brochure, 1993.

Boston Scientifice Corporation Pinnacle™ brochure, 1996.

Terumo® Radifocus Introducer II Sheath brochure.

Medikit Supersheath Introducer brochure.

C. R. Bard, Inc. catalog page on Desilets–Hoffman® Catheter Intrroducer Set, Sep. 1984.

*Primary Examiner*—Wynn Wood Coggins
*Assistant Examiner*—Deborah Blyveis
*Attorney, Agent, or Firm*—Sterne, Kessler, Goldstein & Fox, P.L.L.C.

[57] ABSTRACT

A catheter introducer assembly includes an introducer sheath mounted on a dilator. The distal end of the dilator protrudes beyond the distal end of the sheath and defines an arrowhead having a proximally facing surface that cooperates with the distal end of the sheath to reduce the risk of tissue trauma while facilitating smooth entry into and through tissue. The proximal hubs of the dilator and sheath are configured with respect to the relation between the distal end of the dilator and sheath to provide smooth controlled withdrawal of the dilator through the sheath. The sheath is attached, at its proximal end, to a housing with a mechanical connection that does not require the use of adhesives, welding or other bonding techniques. The connection also may incorporate an integral strain relief for the proximal end of the sheath. The housing at the proximal end of the sheath includes a proximal end cap construction that is secure and is easily attached without requiring ultrasonic welding or other bonding techniques. Methods are described for assembling the introducer and for forming the arrowhead portion of the dilator.

19 Claims, 10 Drawing Sheets

U.S. PATENT DOCUMENTS

| | | |
|---|---|---|
| 4,994,027 | 2/1991 | Farrell . |
| 5,011,478 | 4/1991 | Cope . |
| 5,015,239 | 5/1991 | Browne . |
| 5,085,649 | 2/1992 | Flynn . |
| 5,092,857 | 3/1992 | Fleischhacker . |
| 5,098,393 | 3/1992 | Amplatz et al. . |
| 5,215,528 | 6/1993 | Purdy et al. . |
| 5,215,540 | 6/1993 | Anderhub . |
| 5,263,937 | 11/1993 | Shipp . |
| 5,279,610 | 1/1994 | Park et al. . |
| 5,290,245 | 3/1994 | Dennis ................... 604/167 |
| 5,292,311 | 3/1994 | Cope . |
| 5,300,047 | 4/1994 | Beurrier . |
| 5,308,342 | 5/1994 | Sepetka et al. . |
| 5,318,588 | 6/1994 | Horzewski et al. . |
| 5,383,860 | 1/1995 | Lau ......................... 604/167 |
| 5,387,197 | 2/1995 | Smith et al. . |
| 5,496,344 | 3/1996 | Kanesaka et al. . |
| 5,499,975 | 3/1996 | Cope et al. . |
| 5,520,655 | 5/1996 | Davila et al. ............ 604/167 |
| 5,531,699 | 7/1996 | Tomba et al. . |
| 5,545,141 | 8/1996 | Eld . |
| 5,545,150 | 8/1996 | Danks et al. ............ 604/256 |
| 5,554,167 | 9/1996 | Young et al. . |
| 5,556,411 | 9/1996 | Taoda et al. . |
| 5,558,651 | 9/1996 | Crawford et al. . |
| 5,558,652 | 9/1996 | Henke ...................... 604/280 |
| 5,573,517 | 11/1996 | Bonutti et al. . |
| 5,618,272 | 4/1997 | Nomura . |

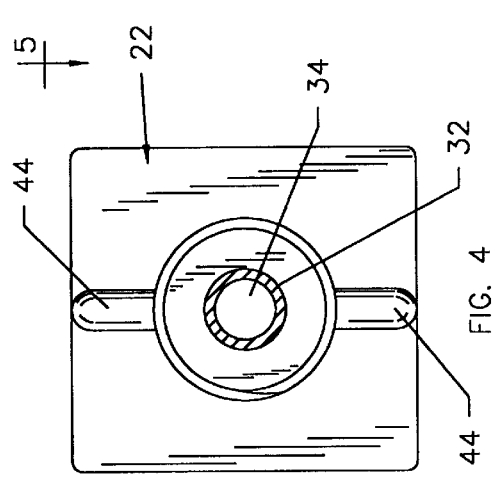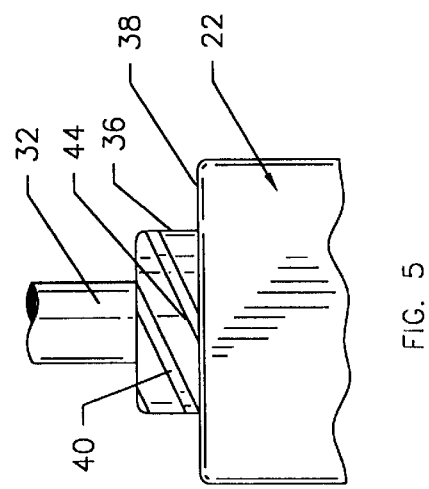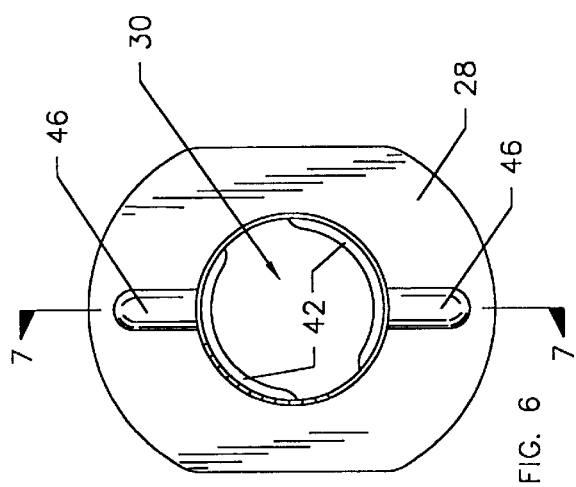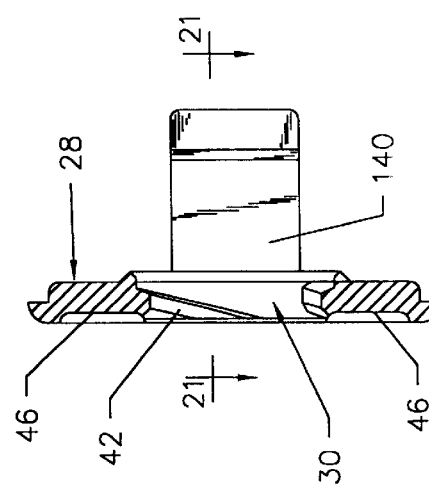

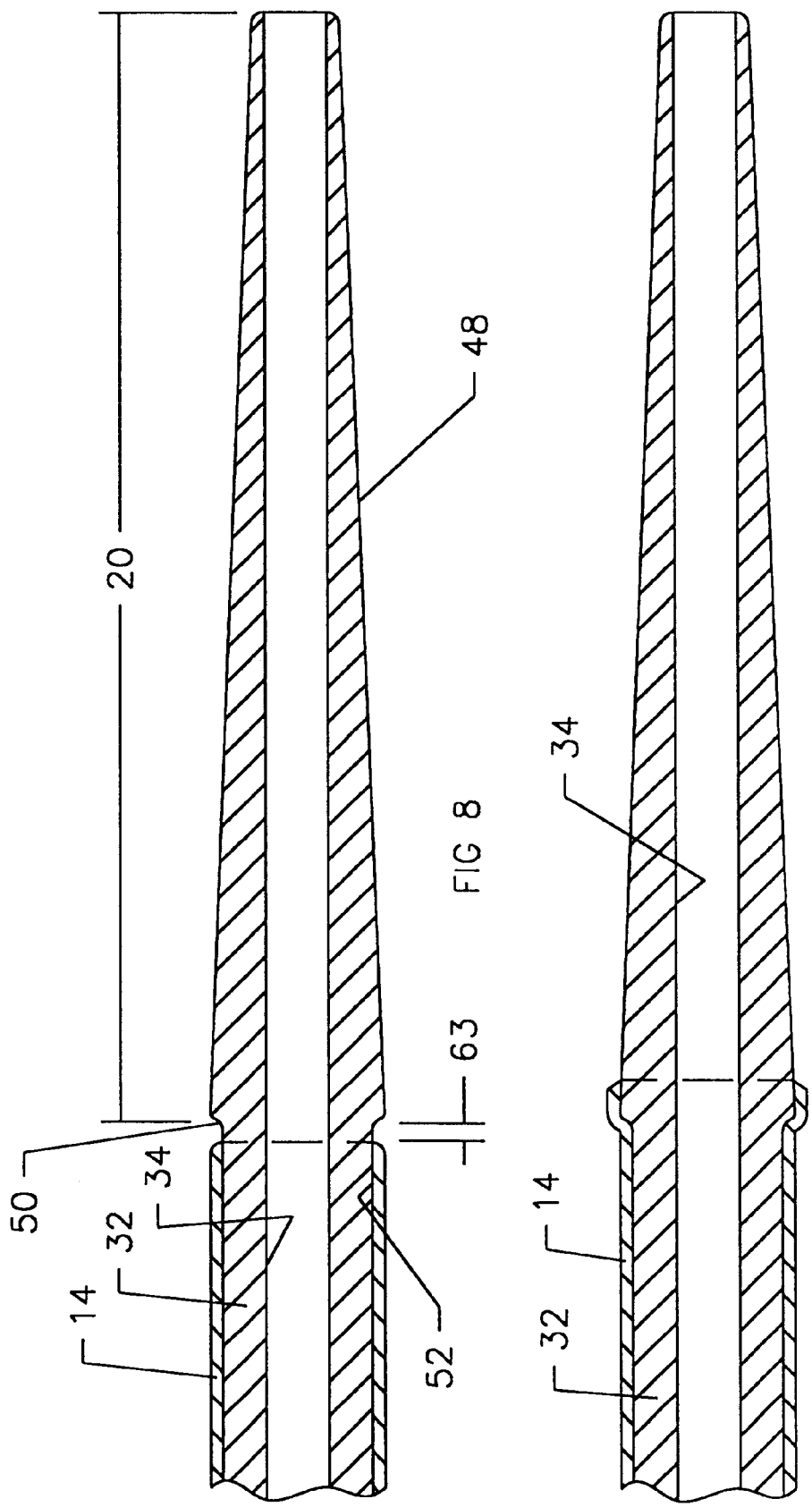

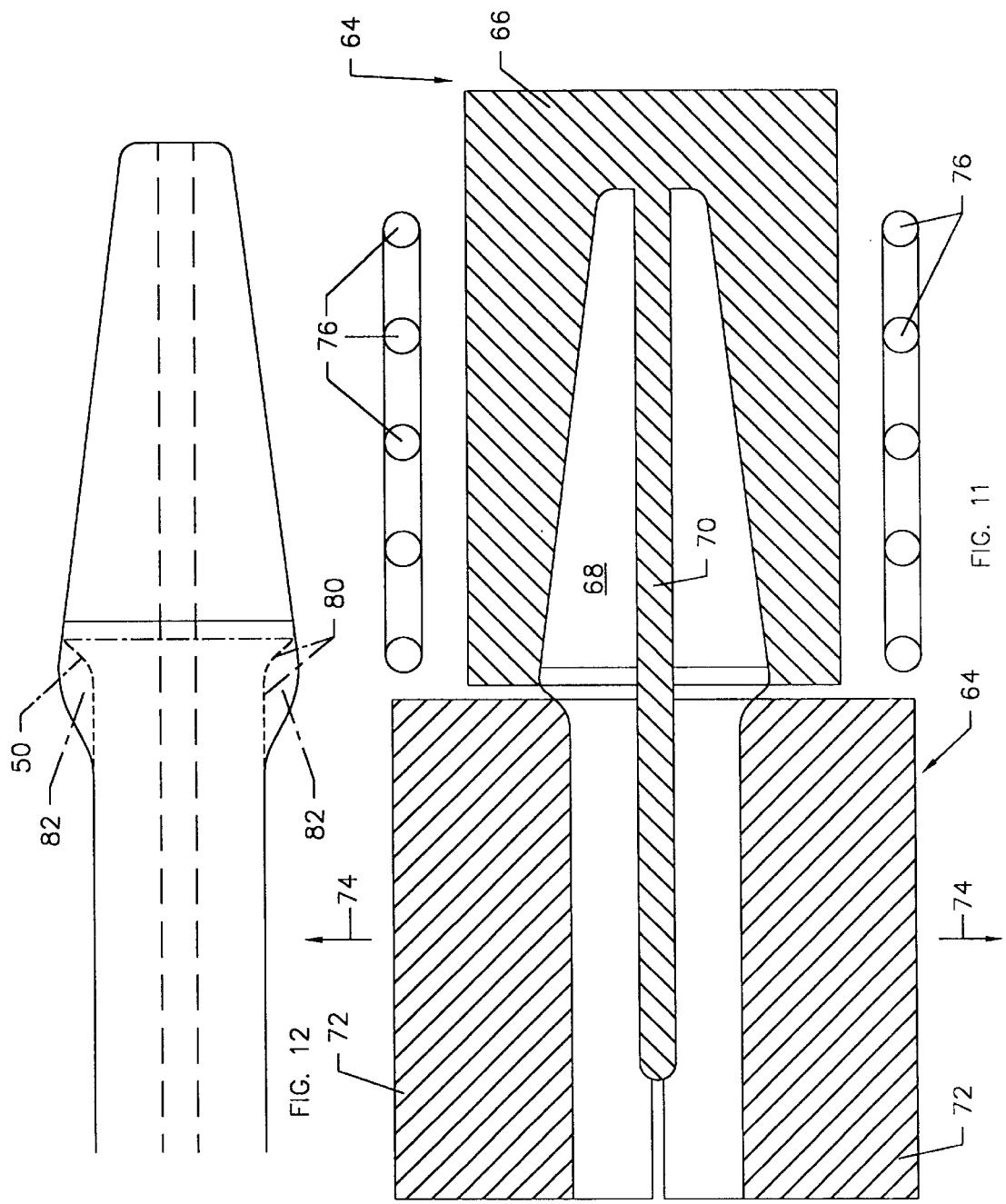

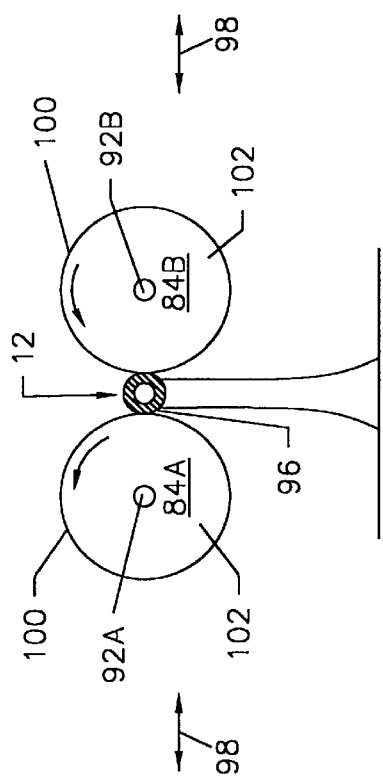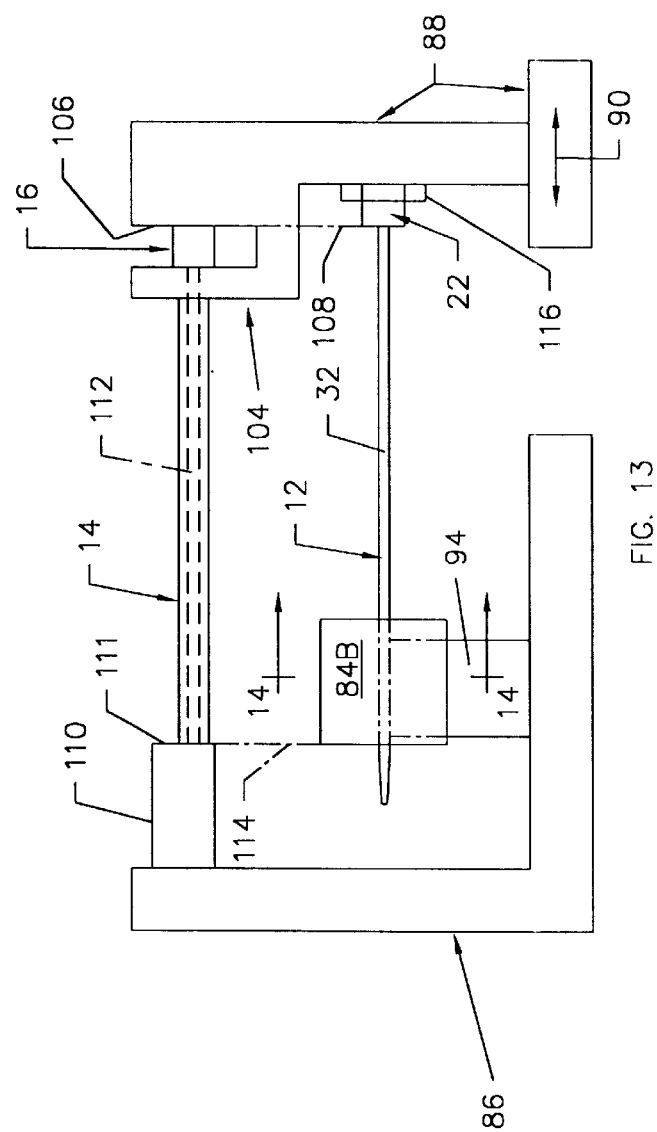

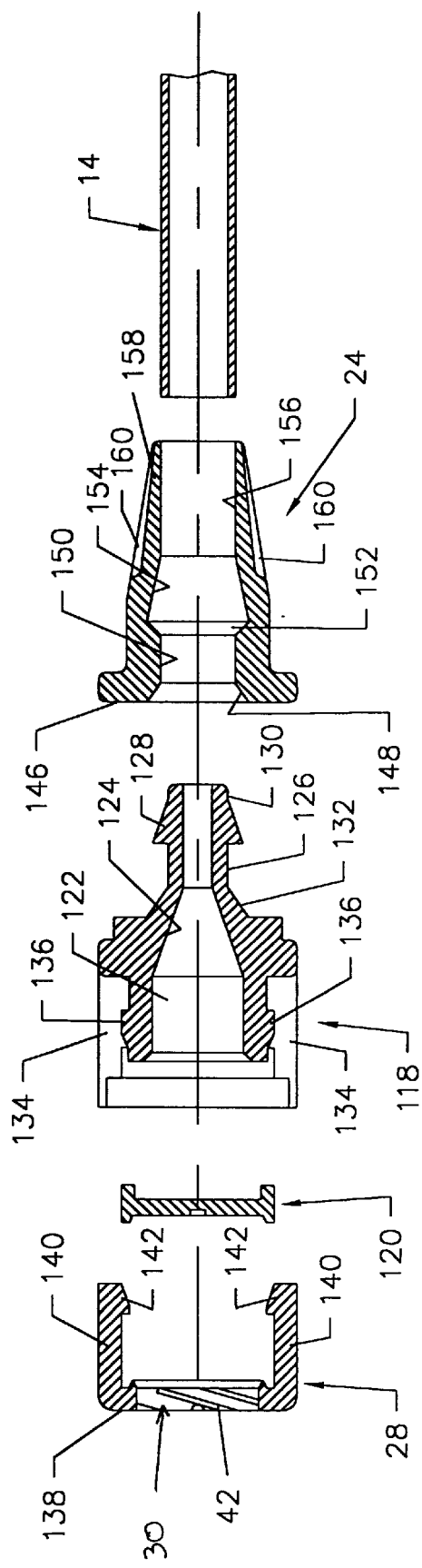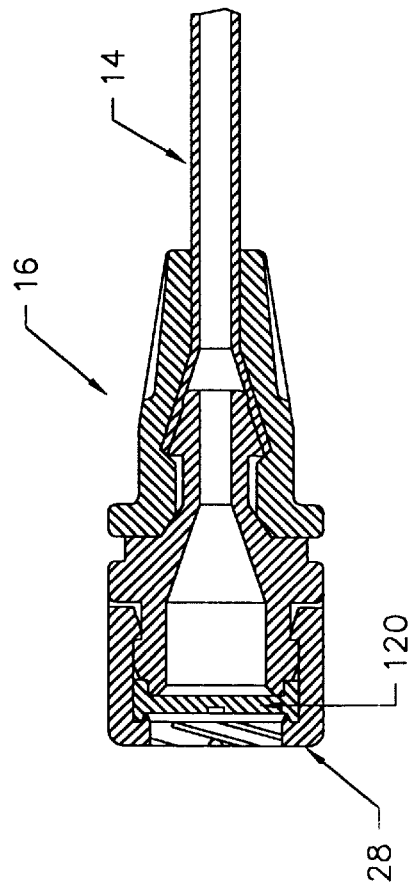
FIG. 17
FIG. 16

CATHETER INTRODUCER

FIELD OF THE INVENTION

This invention relates to catheter introducers and techniques for their manufacture.

BACKGROUND OF THE INVENTION

Catheter introducers are used commonly to provide percutaneous access to a blood vessel in order to facilitate insertion of catheters into and manipulation within the blood vessel without requiring a separate percutaneous or vessel puncture for each catheter. A typical catheter introducer may be considered as having a relatively short tubular sheath, open at its distal end (the end within the patient), and a housing attached to the proximal end (outside of the patient) of the sheath. The housing typically includes a proximal aperture through which a catheter can be passed as well as a self-sealing valve or gasket to effect a seal to prevent blood from leaking out of the introducer, both when a catheter is passed through the introducer as well as when the catheter has been withdrawn from the introducer. The housing also may include a side port through which blood may be sampled or medication or other physiological liquids may be introduced. Such catheter introducers are in common use in angiography and angioplasty as well as other procedures.

The introducer typically is provided in an assembly with a tubular dilator, on which the introducer is mounted. The dilator is longer than the sheath and housing and passes through the housing so that its distal and proximal ends protrude beyond the distal and proximal ends of the sheath and housing, respectively. The distal protruding end of the dilator is tapered to facilitate advancement through tissue. The proximal end of the dilator typically is provided with a hub that is engageable with the housing. The dilator includes a central lumen that extends fully from its proximal to its distal end and receives a guidewire used in connection with percutaneous placement of the catheter-dilator assembly.

Such dilators typically are placed by the Seldinger technique in which a hollow needle first is advanced through the skin, the subcutaneous tissue and into the blood vessel of interest. A guidewire then is advanced through the hollow needle and into the blood vessel. While maintaining that position of the guidewire, the needle then is withdrawn proximally and is separated from the guidewire. With the sheath mounted on the dilator, the dilator then is threaded onto the proximal end of the guidewire and is advanced along the guidewire toward and into engagement with the puncture site. The distal tapered end of the dilator facilitates insertion of the tip of the dilator into the puncture by progressively dilating the puncture as the dilator is advanced through the tissue. Such progressive dilation of the puncture site is intended to facilitate advancement of the still larger diameter introducer sheath into and through the puncture site so that together they can be advanced along the guidewire into the blood vessel. When the distal portion of the sheath has been advanced into the blood vessel, the dilator and guidewire can be removed, leaving the catheter introducer in place and in readiness to receive and direct other guidewires, catheters or other appropriate instruments into and from the blood vessel.

Among the difficulties commonly encountered in the design and use of catheter introducers is to provide a dilator-sheath combination that can be advanced through tissue with minimal patient discomfort and tissue trauma while also avoiding damage to the introducer. Such difficulties typically occur at the transition region between the guidewire and the dilator tip as well as the transition region between the outer diameter of the dilator and the distal end of the sheath. The dilator-introducer sheath assemblies typically present distally facing shoulders at those transitions. Although the radial extent of the shoulders can be minimized by tapering the distal end of the sheath and the dilator to a thin feathered edge, that presents additional difficulties in that the thinning of the wall of the tube increases substantially the risk that the thin edge will curl back when it engages tissue, resulting in substantially increased resistance to advancement and attendant patient discomfort and tissue trauma.

The prior art has recognized these difficulties and has suggested a number of proposed remedies. Among the proposals has been to configure the distal end of the dilator tip to define a proximally facing shoulder behind which the tip of the dilator sheath can be protected as the assembly is advanced through the tissue. For example, U.S. Pat. No. 5,098,393 (Amplatz) and U.S. Pat. No. 5,499,975 (Cope) disclose such introducer assemblies. In general, the object of such arrowhead-like designs is to improve the transition between the sheath and the dilator and, in some cases, between the dilator and the guidewire. Among the difficulties presented by the arrowhead-type of design is that the smoother the transition between the dilator and sheath, the more difficult it is to withdraw the dilator through the sheath and the greater the risk that such withdrawal may damage the tip of the sheath. A very thin, feathered leading edge for the sheath could develop a small split and could break off into the blood stream. The damaged sheath tip could present sharp edges for corners that could injure the delicate inner lining of the blood vessel. A very thin walled delicate tip for the sheath could become bent inwardly, possibly from withdrawal of the dilator, presenting an inwardly projecting sharp edge that could injure a delicate balloon of a balloon catheter or other catheter component adapted to be inserted through the introducer. It would be desirable to provide a dilator-mounted introducer sheath having an arrowhead design for smooth insertion through the tissue in which the assembly can be advanced percutaneously and smoothly to and through the tissue yet in which the dilator can be removed smoothly and with minimal risk of damage to the tip of the sheath. It is among the objects of the present invention to provide such a sheath-dilator configuration as well as improved techniques for making such devices.

Another aspect of the invention relates to the design and construction of the housing at the proximal end of the introducer sheath and the manner in which the two are joined. Catheter introducer housings are employed in the prior art typically have a body and a proximal end cap that mate to engage and secure the hemostasis gasket within the housing. The body typically is connected to the proximal end of the sheath using one or more techniques including heat, ultrasonic bonding, adhesives, insert molding, among others. Representative of such assemblies are described in U.S. Pat. No. 4,000,739 (Stevens), U.S. Pat. No. 4,424,833 (Spector), U.S. Pat. No. 5,304,156 (Sylvanowicz) and U.S. Pat. No. 5,613,956 (Patterson). In general, such prior techniques require the use of special, expensive equipment, such as ultrasonic welders, and can be somewhat labor intensive. Although the desirability of a snap-on proximal end cap has been incorporated into commercial catheter introducers, the snap-on configuration includes a substantially fully circumferential undercut that may present somewhat of a tendency to separate when the device is in use. It would be desirable to provide an improved, more secure connection between the proximal end cap and the body of the housing. More generally, it would be desirable to provide an improved housing design for a catheter introducer that facilitates more efficient, simplified manufacture and assembly of catheter introducers.

SUMMARY OF THE INVENTION

In one aspect of the invention, the distal end of the dilator is formed to include an enlarged diameter dilating member that may be formed in somewhat of an arrowhead-like configuration having a relatively long, distally facing taper and a relatively short, proximally facing taper. The sheath is constructed so that when the dilator hub is properly engaged with the housing on the proximal end of the sheath, the distal tip of the sheath will be located in close proximity to the proximal taper of the dilating member. The configuration of the dilating member and, particularly, the proximal taper is such that when the dilator is withdrawn the proximal taper of the dilating member will dilate the distal tip of the sheath progressively and smoothly as it is drawn proximally into the sheath. The dilator may be configured to effect a combined rotary and axial motion during withdrawal of the dilator and, to that end, the dilator hub and sheath housing are connectible in a threaded connection arranged to control the combined rotary and axial motion as the hub and housing are unscrewed. The extent of axial motion of the dilator relative to the sheath that results from the unscrewing of the hub and housing is long enough to assure that the combined rotary and axial motion will continue until the distal end of the sheath has been dilated sufficiently to enable the remainder of the dilator to be easily withdrawn. Preferably, the threading arrangement continues until the distal end of the sheath has been dilated fully to receive the maximum diameter of the dilating member. Such controlled withdrawal of the dilator relative to the sheath results in a smooth, progressive dilation of the distal tip of the sheath with reduced risk of sheath tip damage while providing a configuration that is percutaneously insertable with relative ease and with minimal tissue discomfort and patient trauma.

Another aspect of the invention relates to the technique for making the combined arrowhead dilator-sheath assembly. To that end, the distal end of the dilator may be molded to form the maximum diameter of the arrowhead and the distal taper. The more proximal portion of the arrowhead may be formed to have greater axial length than that of the finished design and may be considered as having an unfinished proximal region. The proximal taper then is finished to match the length of the sheath with which the dilator is to be used.

In a further aspect of the invention, the connection between the proximal end of the sheath and the housing is designed so that the housing and the sheath can be connected simply and without the use of supplemental securing techniques such as heat bonding, ultrasonic welding, adhesives or the like. To that end, the housing that is to be attached to the proximal end of the sheath includes a distally extending hollow nipple that communicates with the interior of the housing and has an external convolution, such as a barb. The proximal end of the tubular sheath is pressed onto the nipple and a flexible, one-piece, distal cap is slid proximally over the sheath into engagement with the housing body. The distal cap is configured internally to snap-fit about the barbed portion of the nipple thereby securely capturing the proximal end of the sheath between the cap and the nipple. The resulting assembly provides a secure connection without the use of supplemental prior art attachment techniques referred to above. The distal cap advantageously may be formed integrally with a distal extension that serves as a strain relief to surround and provide support for a proximal portion of the sheath that extends beyond the nipple. The strain relief extension can be molded to a distally tapering configuration to provide a progressive transition from maximum to minimum strain relieving support between the rigid housing body and the sheath.

Among the objects of the invention are to provide an improved catheter introducer and dilator assembly that facilitates the ease with which the assembly can be introduced percutaneously through tissue; to provide a catheter introducer assembly in which the transition in the region of the dilator and distal tip of the sheath is configured to facilitate percutaneous insertion with reduced patient discomfort and tissue trauma; to provide an improved catheter introducer construction in which the distal end of the introducer sheath can be provided with a thin wall yet in which the risk of tip damage either from insertion through tissue or withdrawal of the dilator is reduced; to provide a catheter introducer assembly in which the distal tip of the introducer sheath is protected behind an enlarged arrowhead-like member at the distal end of the dilator and in which withdrawal of the dilator through the distal tip of the sheath is effected by controlled combined axial and rotary motion; to provide improved methods for forming the components of the catheter introducer assembly; to provide a connection between the proximal end of a catheter introducer sheath and a housing by which the two can be securely connected without the use of supplemental bonding; and to provide an improved design for the connection between the proximal end of a sheath and the proximal body of a catheter introducer that includes a combined distal cap and strain relief.

DESCRIPTION OF THE DRAWINGS

The foregoing and other objects and advantages of the invention may be appreciated more fully from the following further description thereof, with reference to the accompanying drawings wherein:

FIG. 4 is a partly sectional illustration of the dilator as seen along the line 4—4 of FIG. 2;

FIG. 5 is an illustration of the dilator as seen from 5—5 of FIG. 4;

FIG. 6 is an end view of the proximal face of the proximal end cap of the sheath housing;

FIG. 7 is a sectional illustration of the proximal end cap as seen along the line 7— 7 of FIG. 6;

FIG. 8 is a somewhat diagrammatic sectional illustration of the distal region of the introducer assembly, showing the relationship between the distal end of the sheath and an arrowhead on the dilator when the assembly is in readiness for percutaneous insertion;

FIG. 9 is an illustration similar to FIG. 8 depicting, diagrammatically, the withdrawal of the arrowhead portion of the dilator into the distal end of the sheath;

FIG. 11 is a diagrammatic sectional illustration of a three-piece mold that may be used to form the arrowhead portion at the distal end of the dilator;

FIG. 12 is an illustration, exaggerated for clarity, of the arrowhead tip as it is formed by the mold of FIG. 11 and depicting the relationship of the molded configuration with the intended final configuration of the proximal end of the arrowhead;

FIG. 13 is a schematic side elevation of a fixture for performing a secondary finishing operation on the proximal region of the arrowhead and for matching the dilator with a sheath;

FIG. 14 is a diagrammatic illustration of a portion of the fixture of FIG. 13 as seen along the line 14—14 of FIG. 13;

FIG. 16 is a sectional illustration of the assembly of the housing at the proximal end of the sheath;

FIG. 17 is an exploded sectional illustration of the components of the assembly of FIG. 16;

DESCRIPTION OF THE ILLUSTRATIVE EMBODIMENTS

Figure 1:
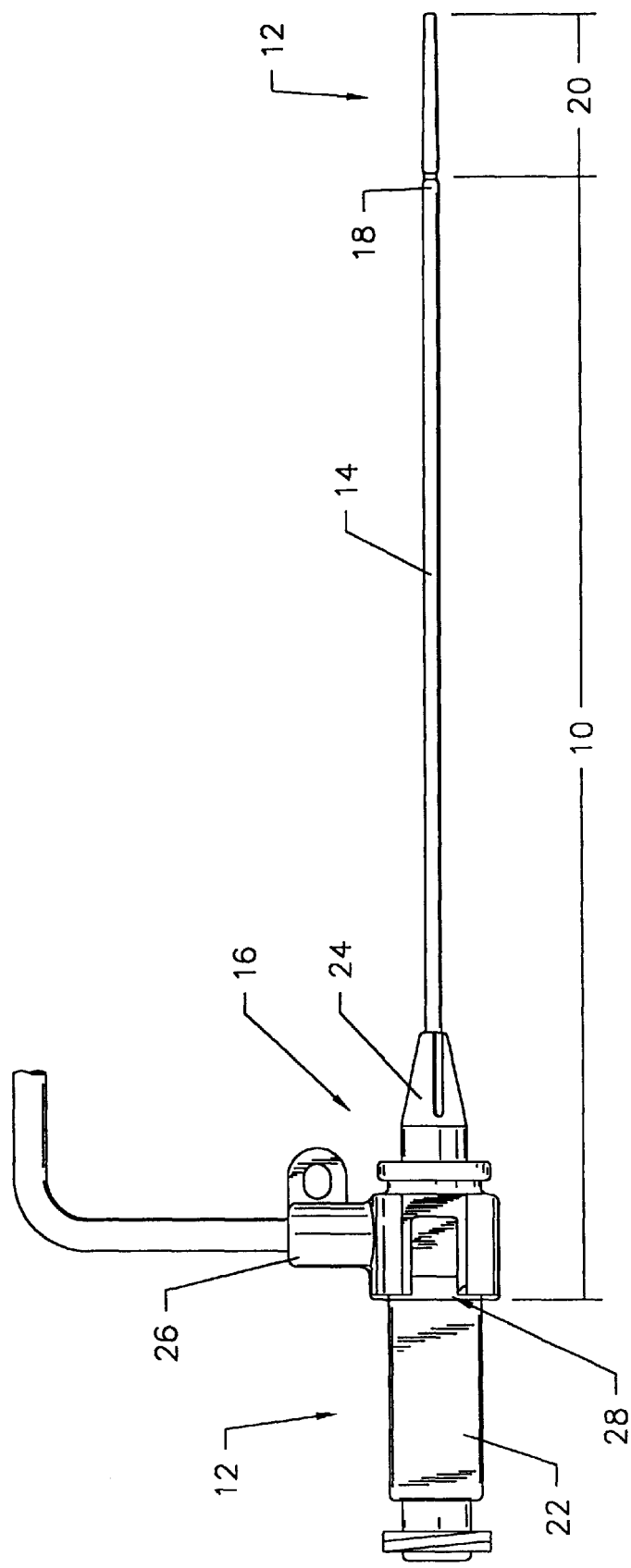
FIG. 1 is a side elevation of a catheter introducer assembly in readiness for percutaneous insertion into a patient.
Figure 2:
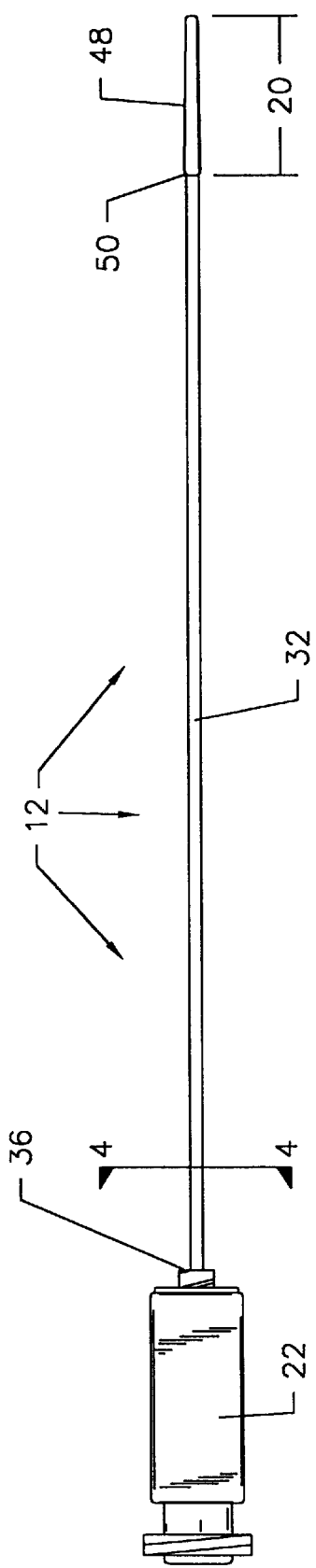
FIG. 2 is a side elevation of the dilator component of the catheter introducer assembly.
Figure 3:
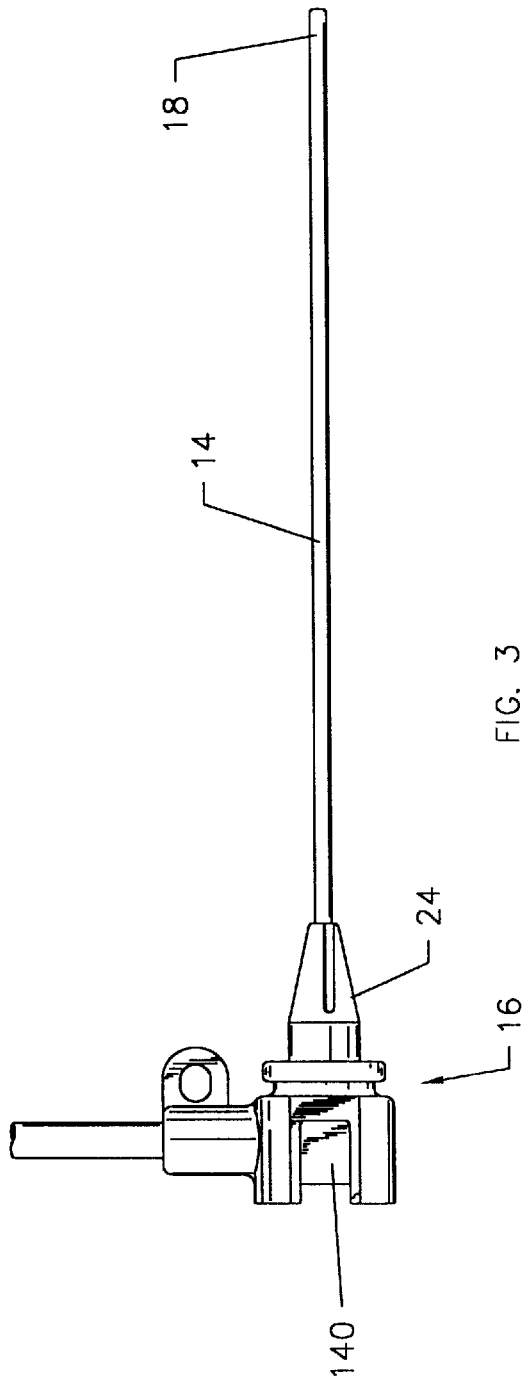
FIG. 3 is a side elevation of the sheath component of the catheter introducer assembly.

FIG. 1 shows a catheter introducer assembly in accordance with the invention. The assembly includes the introducer 10 itself and a dilator 12 that extends through the introducer 10. The introducer 10 includes an elongate flexible polymeric sheath 14 having a housing assembly 16 attached to its proximal end. The distal end 18 of the sheath 14 is open to permit the distal end 20 of the dilator to project through and beyond the distal end 18 of the sheath 14. The proximal end of the dilator 12 includes a hub 22 that is detachably connectible to the housing assembly 16 by a threaded connection, described in further detail below. The housing assembly 16 also includes a distal end cap 24 that may include a flexible strain relief member. A side port 26 through which liquid (e.g., heparin, medication) may be administered or blood may be withdrawn also may be formed as part of the housing. The proximal end of the housing assembly 16 is closed by a proximal end cap 28 having an aperture 30 (FIG. 6) through which the dilator 12 and, subsequently, catheters and the like, may pass. As described in further detail below, a self-sealing gasket 32 (FIGS. 16–17) is contained within the housing assembly 16 and serves to form a seal to prevent back bleeding through the housing, both when a catheter is in place as well as in the absence of a catheter.

The dilator 12 includes an elongate tubular shaft 32 having a central lumen 34 adapted to receive a guidewire during the percutaneous placement of the device, as by the Seldinger technique. The hub 22 also includes an externally threaded projection 36 that extends from the distal face 38 of the hub 22. As described below in further detail, the external threads 40 on the projection 36 are adapted to mate with female threads 42 formed in the end cap 28 of the introducer housing 16 (FIGS. 6–7). The distal face 38 of the hub 22 also may be provided with one or more distally facing detents, such as the radially extending, distally projecting detent elements 44. As described below, the male detent elements 44 engage, in a snap-in fashion, corresponding female detent sockets 46 on the end cap 28 of the housing assembly 16. The snap-fit desirably can be felt by the physician.

The dilation member at the distal end of the dilator is formed to have a larger maximum diameter than the more proximal portions of the dilator shaft 32. The dilator may be arrowhead-like in shape, is formed to include an elongate, relatively gentle distal taper 48 and, at its proximal end, a sharper, short proximal taper 50. An intermediate transitional region 49 between the tapers 48, 50 may be cylindrical and may be of variable length. The inner lumen 58 at the distal end of the sheath 14 is configured to surround and engage the outer surface of the dilator shaft 32. The outer diameter of the distal end of the sheath 14 is selected in relation to the maximum outer diameter defined by the proximal taper 50 so that as the assembly is advanced over a guidewire percutaneously through the skin and subcutaneous tissue, there will be little or no radial extension of the dilator, that is, little or no portion at the distal end of the sheath 14 that projects radially beyond the maximum diameter of the arrowhead. Consequently, when the assembly is advanced through the skin and tissue, the tissue is not exposed to an abrupt, larger diameter shoulder that might increase the resistance to insertion as well as patient discomfort and tissue trauma. It may be noted that when the dilator and sheath are assembled in their insertion configuration, the distal tip of the sheath may be spaced slightly from the proximal taper 50 of the arrowhead. In accordance with the invention, however, the gap is sufficiently small so that when the assembly is passed through tissue, the tissue will not have had time to relax and contract into the region of the gap. The tissue contraction is not immediate so that once the tissue has been dilated to the maximum diameter by the arrowhead, it will not constrict before the distal end of the sheath 14 has had an opportunity to pass through the dilated opening. Therefore, some space between the proximal taper and the distal end of the dilator sheath is permissible. After the assembly has been advanced into the blood vessel, the dilator then is withdrawn while maintaining the sheath 14 in position. Engagement of the proximal taper of the dilator with the distal end of the sheath is suggested, diagrammatically, in FIG. 9

Figure 10:
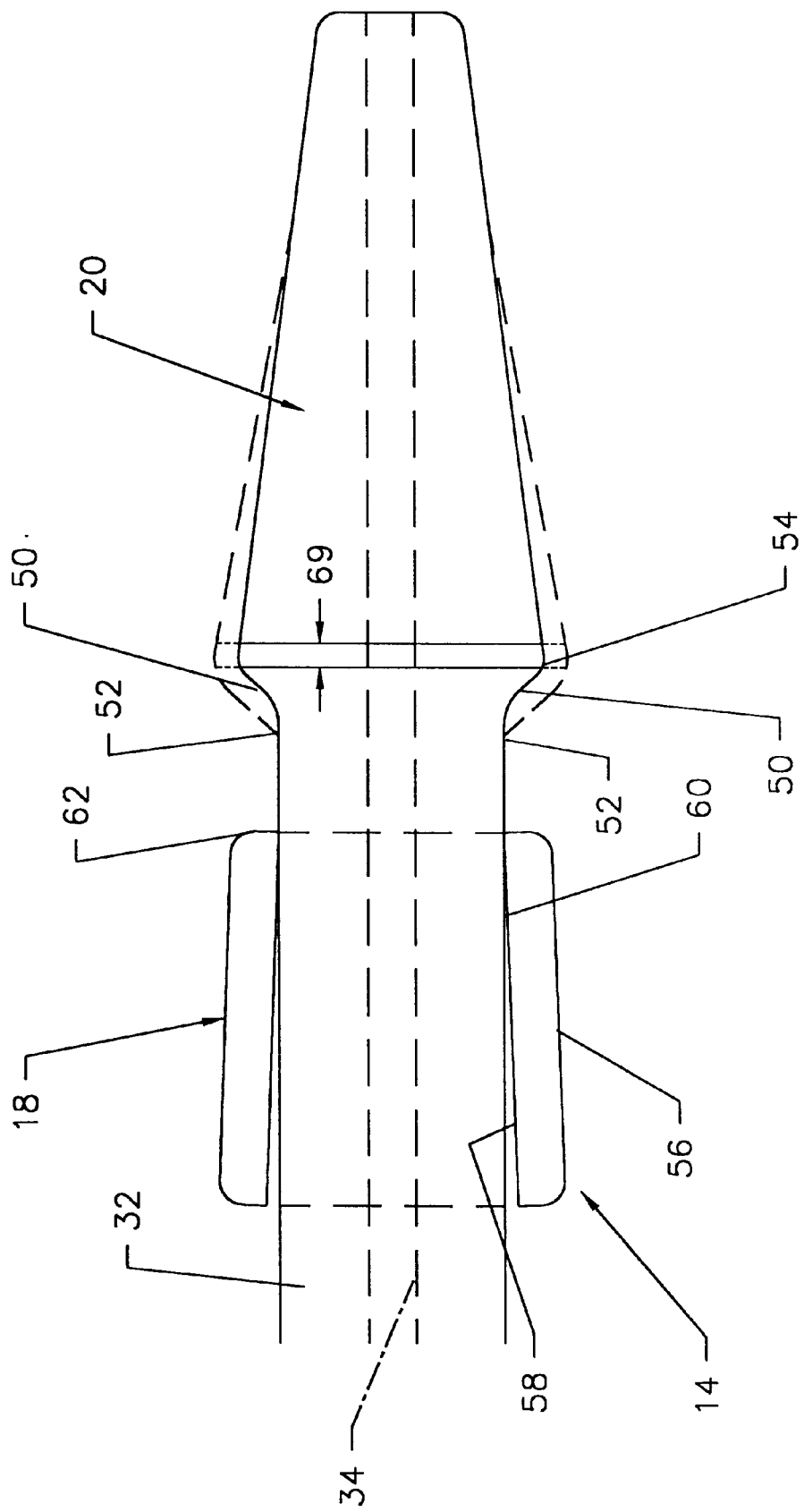
FIG. 10 is an enlarged illustration, partly in approximate scale, depicting the geometry and relationship of the distal end of the sheath with the proximal region of the arrowhead portion of the dilator.

FIG. 10 illustrates, in enlarged, approximately partially scaled detail, the relation between the radial protrusion defined by the arrowhead and the cross-sectional dimensions of the sheath 14 associated with the arrowhead. The rearwardly projecting surface of the proximal taper 50 defined by the arrowhead 20 is defined by a pair of reverse radii, including an inner radius 52 and an outer radius 54, each of the radii being about 0.001 to 0.002 inch in magnitude. The proximal taper 50, defined between the inner and outer radii 52, 54 is sloped at an angle, preferably about 45°, to the longitudinal axis of the dilator (90° cone angle and defines an annular ramp for the distal end of the sheath 14.

The geometry at the distal end 18 of the sheath 14 includes an outer surface 56, an inner surface 58 that includes a dilator-engaging segment 60, and an end face 62. The sheath 14 may be formed from a suitable polymer such as Teflon (polytetrafluoroethylene) having a wall thickness of about 0.008 inch, although tubing formed from a more easily stretched polymer, such as PEBA, commercially available under the trade designation Pebax from the Atochem Company, having a greater wall thickness of about 0.010 inch may be preferred because it is more easily stretched by the arrowhead when the dilator is withdrawn proximally. The wall thickness at the distal extremity of the sheath, defined at the region of the end face 62, is somewhat thinner than at the more proximal portions of the sheath. Although it is desirable that the wall thickness at the distal end of the sheath (i.e., at end face 62) is as close to the extent of radial projection of the arrowhead from the outer diameter of the dilator shaft 32 as can be practically manufactured, some radial projection of the sheath beyond the maximum radial projection of the arrowhead may be tolerated up to a maximum of about 0.002 inch. Preferably, the wall thickness at the distal extremity of the sheath, just proximally of the end face 62 may be of the order of 0.003 inch.

The catheter introducer assembly is constructed so that the end face 62 of the sheath will remain spaced from the proximal taper 50 of the dilator. By way of example, the gap 63 may be within the range of about 0.002 to about 0.030 inch, preferably in the range of 0.002 to about 0.20 inch, as measured from the inner radius 52 of the arrowhead to the end face 62 of the sheath, with a nominal gap 63 of the order of 0.010 inch. The outer surface 56 of the sheath 14, at the distal end 18 may be tapered, as by having been molded or by a taper grind, along a length of about 0.25 inch. Additionally, the corner at the end wall 62 and the outer surface 56 of the sheath preferably is heated sufficiently to form a somewhat rounded corner.

Dilators in accordance with the invention may be made most commonly in a size range of 4 French to 9 French, although other sizes outside of that range also may be made. For dilators within the 4 French to 9 French range, the dilator shaft may have an outer diameter of between about 0.057 to about 0.122 inch, a guidewire lumen diameter of between about 0.27 to about 0.40 inch, an arrowhead length, as measured from the outer radius 54 to the distal tip of the dilator of about 0.750 inch for all sizes and a maximum diameter for the dilator, at the transition region 49 between the proximal and distal tapers 50, 48 of between about 0.062 to about 0.129 inch. The distal tip of the arrowhead 20 preferably is radiused (e.g., 0.005 inch). The diameter at the distal tip of the arrowhead at the beginning of the radiused portion may be between about 0.042 inch to about 0.052 inch for the 4 French to 9 French range of sizes, the range of variation being suggested in phantom at 61 in FIG. 10.

When withdrawing the dilator 12 axially through the sheath 14 in accordance with the invention, it is preferred to simultaneously rotate the dilator relative to the sheath. In accordance with the invention the rotation and axial withdrawal are controlled to achieve uniform results. To that end, the hub at the proximal end of the dilator 12 and the housing 16 of the sheath assembly are threadably connected by engagement of threaded projection 36 on the dilator hub 22 with female threads 40 on the proximal face of the housing 16. The pitch of the threads is selected to control the relative rate of axial withdrawal and angular rotation. The arrangement of the snap-fit male and female detent components 44, 46 provides a tactile indicator to the physician when the hubs are fully connected. When the dilator hub 22 is unscrewed relative to the sheath housing 16, the dilator is withdrawn rearwardly to cause the tip 18 of the sheath 14 to be dilated and ride over the proximal taper 50 of the arrowhead 20, as suggested in FIG. 9. The dynamics of the device are understood to be such that as the arrowhead is drawn rearwardly into engagement with the distal face 62 of the sheath 14, the ramp defined by the generally conical proximal taper 50 of the arrowhead will progressively and substantially uniformly circumferentially stretch the distal end of the sheath to permit the arrowhead to be progressively withdrawn into the sheath, eventually drawing the full diameter of the arrowhead into the sheath. The configuration of the screw threads 40, 42 is selected to assure that they will maintain their engagement during the full range of linear motion necessary to take up the clearance between the end wall 62 of the sheath and the beginning of the proximal taper 50 (as defined at the inner radius 52). Preferably the threads 40, 42 are arranged to provide combined axial and rotary motions sufficient to assure that the full circumference of the tip of the sheath respectively engages the outermost circumference of the arrowhead. Preferably, the threads are designed to provide a linear motion of about 0.050 inch, substantially more than the range of spacing (0.002 to 0.030 inch) of the clearance between the dilator and the arrowhead. Additionally, it is understood that the mechanical advantage provided by the threaded coupling of the dilator hub and sheath housing results in a substantially smoother action requiring substantially less applied force as compared with a device in which an arrowhead dilator is simply pulled axially out of the sheath. By maintaining the outer diameter of the end face 62 of the sheath very close to, if not identical, to that of the arrowhead, the risk of the distal end of the sheath becoming caught on tissue is significantly reduced.

FIGS. 11–14 illustrate, diagrammatically, a simplified, yet preferred, technique for forming the dilator and matching it to the sheath to assure proper positioning of the distal end 62 of the sheath 14 with respect to the proximal taper 50. The dilator is formed from an extruded tube of appropriate polymeric material, such as high density polyethylene. FIG. 11 shows, diagrammatically, a preferred mold for forming the arrowhead configuration at the distal end of the dilator. The mold includes a primary section 66 having a mold cavity 68 configured to define the shape of the elongate distal taper and the intermediate transition section 49. The mold primary section 66 also includes a central mandrel 70 that projects proximally out of the mold cavity 68. The open end of the mold cavity 68 is closed by a pair of proximal mold sections 72 that are movable between the closed mold configuration shown in FIG. 11 to an open configuration in which the sections 72 have been moved apart as suggested by the arrows 74. The mold sections 72 can move apart to permit insertion and removal of the tube. Although the mold surfaces defined by the mold cavity 68 in the primary mold section 66 are designed to form the final configuration of its associated portions of the dilator, the proximal mold sections 72 are designed only to form the proximally facing region of the arrowhead sufficiently to prepare it for a secondary finishing operation. In accordance with the invention, the proximal mold sections 72 are configured to form the proximally facing surfaces of the arrowhead to be oversized when removed from the mold so that when finished in a subsequent operation the dilator will conform and fit accurately with the specific sheath with which the dilator is to be coupled. FIG. 12 illustrates a portion of a dilator after it has been removed from the mold, showing its intentionally oversized molded shape and, in phantom, the intended final configuration after the secondary operation, described below, has been performed. In order to mold the distal end of the dilator, the tubular blank from which the arrowhead dilator is to be made is inserted into the primary mold section 66 with the mandrel 70 extending into the lumen of the tubular stock. The proximal mold sections 72 then are closed to define the full molding cavity. The mold then is heated, as by induction heating coils. At an appropriate temperature, the dilator tubing material is urged into the mold. The tubing advanced into the mold is softened or melts sufficiently so that continued advancement will cause the mold cavity to fill and reform the end of the tube in the arrowhead shape. After appropriate cooling, the mold is opened and the dilator is removed in readiness for the secondary finishing operation.

Figure 15:
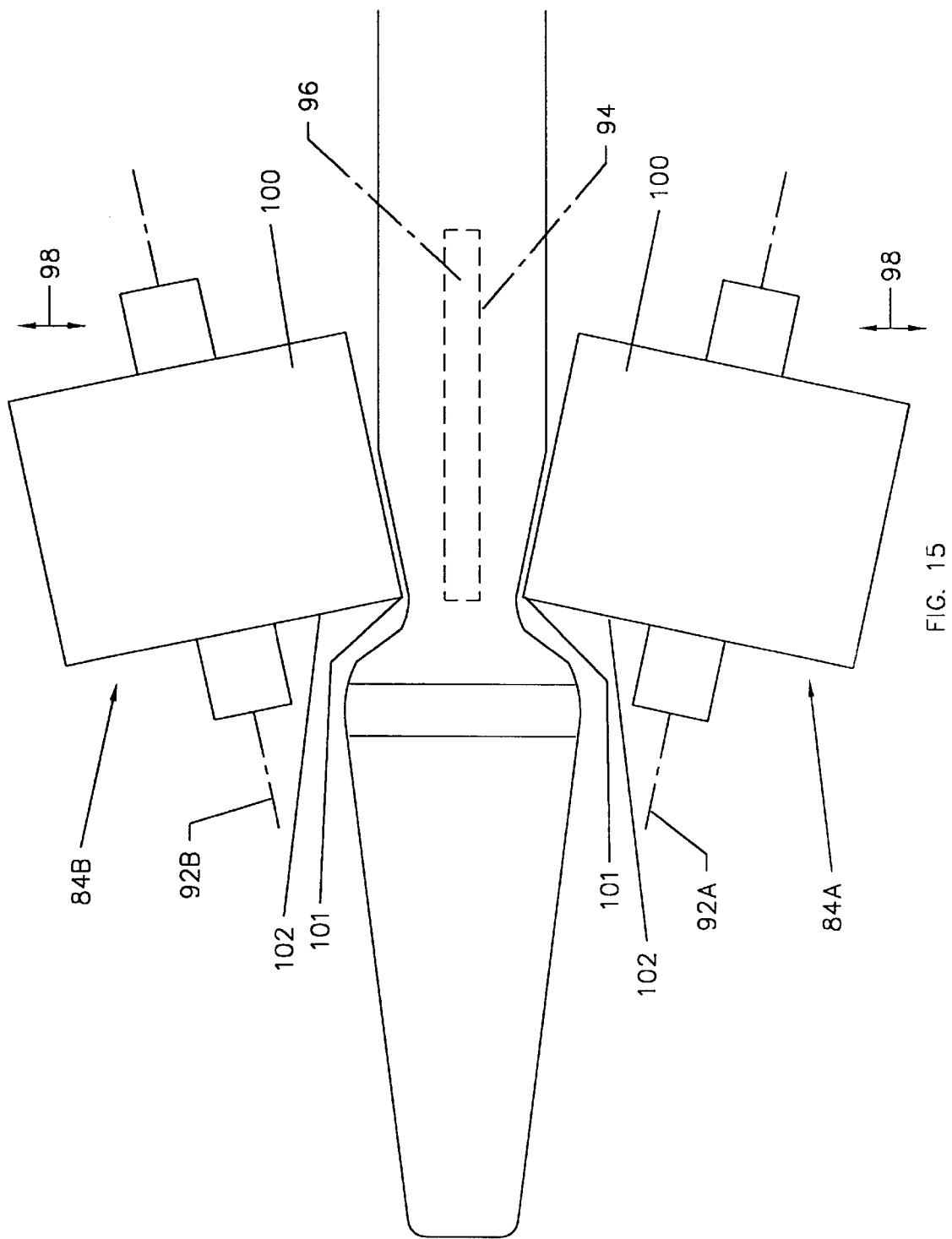
FIG. 15 is a somewhat diagrammatic plan view, exaggerated for clarity, of the relationship between the arrowhead-forming rolls and the dilator.
Figure 19:
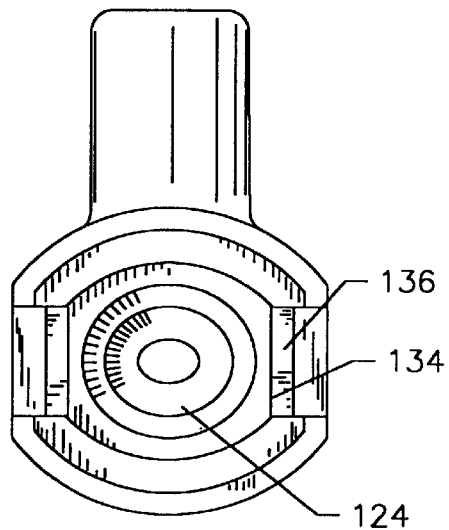
FIG. 19 is an end view, as seen from the left of FIG. 18 of the housing.
Figure 18:
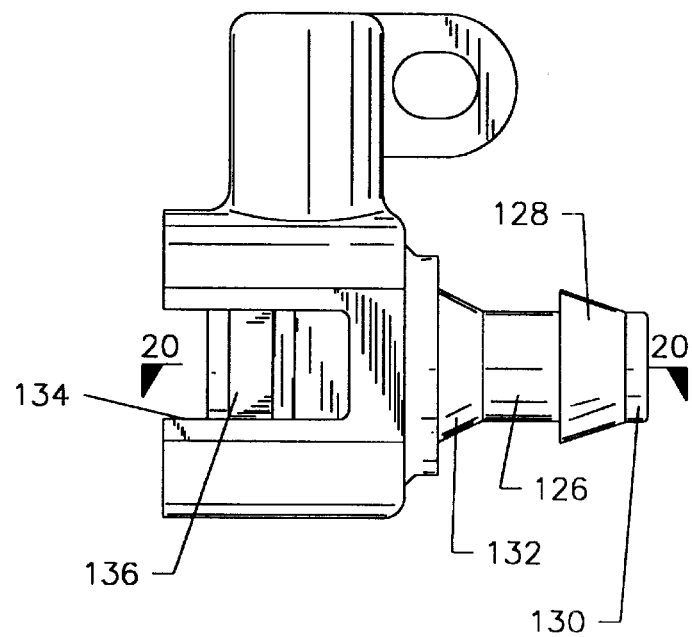
FIG. 18 is a side elevation of the body component of the housing.
Figure 21:
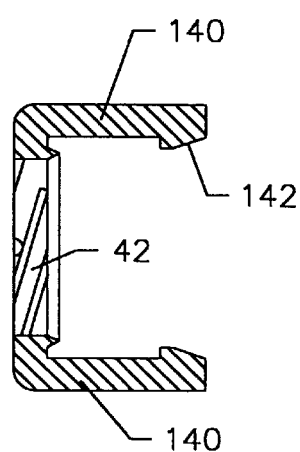
FIG. 21 is a sectional illustration of the proximal end cap, as seen along the line 21—21 of FIG. 7.
Figure 20:
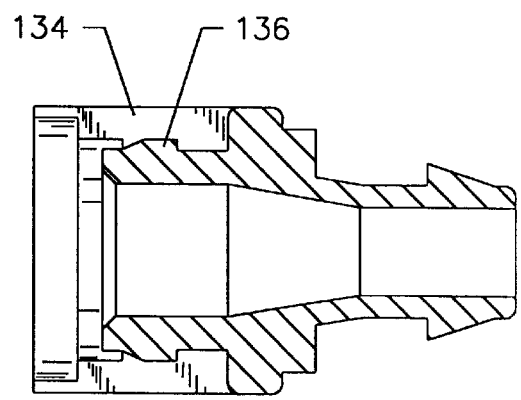
FIG. 20 is a sectional illustration of the body component of the housing as seen along the line 20—20 of FIG. 18.

As shown in FIG. 12, the configuration of the proximal region of the arrowhead is molded to include a generally cylindrical segment 78 that extends proximally beyond the intended final shape of the proximal region, indicated in phantom at 80. The annular region of excess material 82 may be removed or, preferably, reformed to the desired final configuration. FIGS. 13–15 illustrate, diagrammatically, and in exaggerated fashion, a device by which the proximal region of the arrowhead preferably is reformed to the desired shape as well as to locate the proximal taper 50 in the desired position relative to the distal end of the sheath with which the dilator is to be combined. The apparatus is configured to reform the over-molded portion 82 by cold rolling it between a pair of rollers 84. FIG. 13 illustrates, diagrammatically, a fixture for positioning the distal end of the dilator 12 with respect to the rollers 84 in which the sheath 14 with which the dilator 12 is to be combined is used as a gauge to facilitate location of the dilator 12 with respect to the rollers 84. To that end, the fixture may be considered as having a fixed frame 86 and a movable frame 88 that can be adjustably positioned toward and away from the fixed frame 86 as suggested by the arrows 90. The rollers 84 are mounted to the fixed frame 86 for rotation about axes 92A, 92B, respectively, the supporting means for the rolls 84A, 84B having been omitted for clarity. The fixture also may include a supporting anvil 94 having an upper surface 96 on which the dilator shaft can rest while it is being rotated between the rollers 84A, 84B. The support surface 96 of the anvil should be disposed to support the longitudinal axis of the dilator 12 so that it is located directly between the roller axes 92A, 92B. So supported, the rollers will engage the dilator 12 at diametrically opposite location during the cold rolling process.

FIG. 15 illustrates, in highly exaggerated fashion, the orientation of the rolls 84A, 84B with respect to the supported dilator. The rolls 84A, 84B are mounted for relative movement toward and away from each other as suggested by the arrows 98 of FIGS. 14 and 15. The rolls 84A, 84B thus can be opened to receive the molded dilator shaft in readiness for the secondary finishing operation. When the dilator shaft has been properly positioned and is supported on the surface 96 of the anvil 94, the rolls 84A, 84B are closed toward each other. Appropriate stops (not shown) may be provided to gauge the extent to which the rolls 84A, 84B are brought together. Such stops may be adjustable so that the fixture can accommodate different sizes of dilators. Although the rolls may be formed with specially contoured surfaces engageable with the dilator shaft, we have found that rollers having a simple right cylindrical shape may be employed effectively to produce the desired proximal taper 50. Each of the rolls includes a circumferential surface 100 and a distal end face 102 that lies in a flat plane perpendicular to the axis of rotation 92. We have found that by orienting the axes 92A, 92B of the rolls at a slight distally converging angle toward each other, the cylindrical surfaces 100 of the rolls will reform the excess molded material 82 to cause it to cold flow and merge with the adjacent portions of the dilator shaft. The corner junction defined between the surfaces 100, 102 has been found to define the region of the inner radius 52 of the resulting proximal taper. It may be noted that FIG. 15 illustrates, also for exaggerated clarity, the rolls 84A, 84B as being brought together so that their corners 101 are spaced closer than the intended diameter of the dilator shaft. When the rolls are removed, the elasticity of the dilator material enables the dilator shaft to reexpand slightly to maintain a substantially continuous outer diameter proximally of the arrowhead.

In order to assure that the proximal taper is formed at the desired location with respect to the sheath 14 with which it is to be matched, the fixture includes an arrangement for using the sheath 14 to gauge the location where the rolls 84A, 84B engage the dilator shaft. To that end, the movable frame 88 may include a housing support 104 adapted to engage the housing 16 of the introducer sheath, with the proximal face of the housing 16 in engagement with a reference surface 106 that lies along a reference plane 108. The fixed frame 86 includes an abutment 110 with a sheath support mandrel 112 secured to and extending from the abutment 110. The housing support 104, abutment 110 and support mandrel 112 are arranged so that the sheath 14 can be placed over the mandrel 112 with its distal tip in contact with a reference face 111 on the abutment 110. The reference face 111 is aligned with a reference plane 114. The rolls 84A, 84B also are aligned with respect to the reference plane 114 so that the surfaces 100, 102 of the rolls will be disposed in a precise location relative to the reference plane 114. The movable frame 88 includes a hub support, indicated schematically at 116, to engage and support the hub 22 of the dilator such that its distal face will be disposed in a predetermined location relative to the reference plane 108. Although with larger sizes of dilators 12, a central support mandrel is not considered necessary, such a support mandrel may be desirable with smaller sizes in order to assure proper support for the dilator during the rolling procedure. It should be appreciated, therefore, that when a sheath 14 has been loaded into the fixture in proper orientation with respect to the reference planes 108, 114, the proximal overmolded region 82 of the molded arrowhead will be located with respect to the rolls 84A, 84B and to the distal end of the dilator 114 to form the final dilator configuration as described above. It should be understood that the fixture may be provided with various adjustments to facilitate proper set-up of the fixture as will be apparent to those skilled in the art.

Another aspect of the invention relates to the manner in which the housing 16 is constructed and is connected to the proximal end of the sheath 14 without requiring techniques conventionally used in the art for that purpose such as ultrasonic welding, heat bonding, adhesives, insert molding or the like. As shown in FIG. 17, the housing 16 include a body 118, a proximal end cap 28 attachable to the proximal end of the body, a hemostasis gasket 120 and a distal end cap 24 that, preferably, includes an integral strain relief extension. The body 118 may be molded from a suitable relatively hard plastic, such as ABS, to include an internal chamber 122 having a distally tapered portion 124 that transitions into the lumen of a distally projecting nipple 126. The lumen through the body should have a diameter sufficient to permit passage of the arrowhead of the dilator. The outer surface of the nipple 126 is provided with a convolution, such as, for example, a distally tapering annular barb 128 that may terminate in a short tubular tip 130. The external surface of the housing 18 proximally of the nipple 126 preferably is tapered in a generally conical configuration at 132 to provide a secure seat for the distal end cap 24. Longitudinally extending slots 134 preferably are formed along opposed lateral sides of the body 118, the body 118 being further formed to define laterally outwardly projecting detents 136 that extend into the slots 134. The proximal region of the body 118 is formed to receive the hemostasis gasket 32. By way of example, the hemostasis gasket 32 may take any of a number of forms, such as those described in U.S. Pat. No.

4,424,833 (Spector), U.S. Pat. No. 5,304,156 (Sylvanowicz), among others.

The proximal end cap 28 also may be molded from ABS polymer and includes an end wall 138 and a pair of distally extending, laterally spaced prongs 140, each of which terminates in a detent element 142 adapted to engage, in a snap-fit, one of the detent elements 136 on the body 118. The prongs 140 are laterally flexible so that they can be advanced along the slots 134 and flexed to engage the detents 136 as shown in the assembly of FIG. 16. The internally facing surfaces of the end cap 28 and body 118 are configured to engage the particular hemostasis gasket 32 selected for the introducer.

The sheath is attached to the housing 16 by slipping the proximal end of the tubular sheath 14 onto the barbed nipple 126 and then sliding a distal retention cap 24 over the connected sheath and nipple to secure the assembly together. The retention cap 24 is illustrated as being formed integrally with a distal extension 158 that serves as a strain relief to resist kinking of the sheath at its connection with the body 118. In the illustrative embodiment, the distal end cap 24 and strain relief 158 incorporated as an integral single unit may be molded from a suitable relatively flexible elastomeric polymer such as Pebax. The distal end cap is molded to include a central lumen configured to mate with distal portions of the housing 118. To that end, the proximal end of the end cap 24 is formed to define a circumferential flange 144 having a planar surface 146 and a conical surface 148 adapted to mate with the corresponding surfaces, including conical surface 132, on the body 118. The conical surface 148 of the end cap transitions to a cylindrical segment 150 that, in turn, leads to a succession of segments corresponding to the convolutions about the nipple 126 to cooperate to secure the proximal end of the sheath, as described below. In the illustrative embodiment, the internally defined segments include a diverging segment 152, a converging segment 154 and a cylindrical segment 152. The cylindrical, diverging and converging segments 150, 152,154 are configured to receive the nipple and annular barb 128 with minimal clearance sufficient to entrap the proximal end of the sheath 14 that is disposed on the nipple. Preferably, the distal cap 24 is molded to conform relatively closely to the configuration of the barbed nipple. The relatively flexible, elastic characteristic of the material from which the end cap is formed enables it to expand as it is forced over the combined sheath and nipple, the cap 24 thereafter contracting and serving to maintain the sheath tightly about the convolutions of the barbed nipple in secure engagement. The distal portion of the distal cap 24 may include an extension 158 that defines the cylindrical segment and that serves as a strain relief to provide adequate support at the juncture of the sheath 14 with the body 118. The extension 158 is generally tubular and preferably is provided with a progressively decreasing wall thickness and outer diameter in a distal direction. The flexibility may be modified further by forming slots or ridges 160 about the exterior of the strain relief extension 158.

When assembling the sheath and body, the distal cap 24 is placed onto the sheath 14. The proximal end of the sheath then preferably is softened and mechanically flared to facilitate its engagement and fitting onto the barbed nipple 126. When the sheath 14 has been advanced fully onto the barbed nipple 126, the distal cap 24 and integral strain relief are forced proximally over and about the assembled sheath and nipple as shown in FIG. 16. The resulting connection is secure and does not require supplemental bonding, insert molding or the like. Additionally, the cap 24 provides an integral strain relief to support the sheath and resist kinking.

From the foregoing, it will be appreciated that the invention provides a catheter introducer system, and components thereof, that improve the ease with which the introducer sheath can be advanced through tissue while providing a reduced risk of trauma to the tissue. The combination of the dilator and sheath includes a configuration in which the relatively fragile distal end of the sheath engages the distal end of an arrowhead-type dilator in a controlled manner that minimizes the risk of damage to the tip of the sheath. The invention also provides a structure for the sheath and its housing that simplifies assembly of the components for the housing and a strain relief while providing secure retention of the proximal end cap and enabling the housing to be assembled in a less labor intensive procedure.

It should be understood, however, that the foregoing description of the invention is intended to be merely illustrative thereof and that other embodiments, modifications and equivalents may be apparent to those skilled in the art without departing from the spirit and scope of the invention.

Having thus described the invention, what we desire to claim and secure by Letters Patent is:

1. A catheter introducer assembly comprising:

an elongate tubular single layer sheath including proximal and distal ends, said sheath having a housing with an aperture at its proximal end;

a dilator having an elongate shaft including proximal and distal ends said dilator having a hub at its proximal end, the shaft extending though the aperture, the housing and the tubular sheath;

the distal end of the dilator having a radially enlarged dilation member having a proximally extending taper and a substantially uniform distally extending taper;

the housing and the hub being detachably connected to each other; and the sheath having a length such that when the housing and the hub are fully connected, the distal end of the sheath is disposed proximally of the proximally extending taper of the dilation member and is in contact with the dilator shaft.

2. A catheter introducer assembly comprising:

an elongate tubular sheath including proximal and distal ends, said sheath having a housing with an aperture at its proximal end;

a dilator having an elongate shaft including proximal and distal ends, said dilator having a hub at its proximal end, the shaft extending though the aperture, the housing and the tubular sheath;

the distal end of the dilator having a radially enlarged dilation member having a proximally facing surface and a distally facing surface;

the housing and the hub being detachably connected to each other; and the sheath having a length such that when the housing and the hub are fully connected, the distal end of the sheath is disposed proximally of the proximally facing surface of the dilation member and is in contact with the dilator shaft;

wherein the housing and the hub are threadably connected to cause simultaneous rotary and axial motion of the dilator relative to the sheath during detachment and withdrawal of the dilator at least during an initial portion of said detachment and dilator withdrawal.

3. A catheter introducer assembly as defined in claim 2, further comprising a space between the distal end of the sheath and the proximally facing surface of the dilation member and wherein said axial motion of said initial portion of said detachment and dilator withdrawal is greater than an axial length of said space.

4. A catheter introducer assembly as defined in claim 3, wherein said axial motion is at least as long as a distance from the distal end of the sheath to a region of maximum diameter of the dilation member.

5. A catheter introducer assembly as defined in claim 1, wherein the distal end of the sheath terminates at an end wall having a radial extension not substantially more than a radial extension defined at a maximum diameter of the dilation member.

6. A catheter introducer assembly as defined in claim 1 wherein the distal end of the sheath terminates in an end wall having a radial extension of not more than about 0.002 inch beyond a radial extension of the dilation member at a region of its maximum diameter.

7. A catheter introducer assembly as defined in claim 1, wherein the tubular sheath is formed from a material that is softer than a material from which the dilator is formed, and the dilation member is larger in diameter than an inner diameter of at least a portion of the sheath.

8. A catheter introducer assembly as defined in claim 2 wherein:
   the distally facing surface of the radially enlarged dilation member comprises an elongate distal taper;
   the proximally facing surface of the radially enlarged dilation member comprises a proximal taper substantially shorter than the distal taper; and
   a region of transition from the proximal taper to the distal taper defines a maximum diameter of the radially enlarged dilation member.

9. A catheter introducer assembly as defined in claim 8 wherein the proximal taper defines a cone angle of about 90°.

10. A catheter introducer assembly as defined in claim 9 wherein the radial extension of the maximum diameter of the radially enlarged dilation member beyond the diameter of the dilator shaft is not substantially more that about two to three thousandths of an inch.

11. A catheter introducer assembly as defined in either one of claims 8 or 9 wherein a space between the distal end of the sheath and the proximally facing surface of the dilation member is in the range of about 0.002 to about 0.030 inch and the radial extension of the distal end of the sheath is up to about 0.002 inch beyond the radial extension at the maximum diameter of the dilation member.

12. A catheter introducer assembly as defined in either one of claims 8 or 9 wherein a space between the distal end of the sheath and the proximally facing surface of the dilation member is in the range of about 0.002 to about 0.020 inch and the radial extension of the distal end of the sheath is up to about 0.002 inch beyond the radial extension at the maximum diameter of the dilation member.

13. A catheter introducer assembly as defined in either one of claims 8 or 9 wherein a space between the distal end of the sheath and the proximally facing surface of the dilation member is about 0.010 inch and the radial extension of the distal end of the sheath is up to about 0.002 inch beyond the radial extension at the maximum diameter of the dilation member.

14. A catheter introducer comprising:
   an elongate tubular sheath having proximal and distal ends;
   a housing attached to the proximal end of the sheath, the housing having a body and a distally extending nipple extending from the body, the proximal end of the sheath being disposed on the nipple and a distal cap snap-fit to the body to capture snugly the sheath between the nipple and the distal cap,
   wherein the nipple has an irregular outer contour and the cap has an inner bore receptive to the irregular contour in a close fit.

15. The catheter introducer as defined in claim 14 wherein the irregular contour comprises the nipple being substantially tubular and having an annular barb disposed about its outer surface.

16. A catheter introducer as defined in any one of claims 14 or 15 wherein the distal cap is formed from an elastic material that is softer and more flexible than that of the body, the cap being adapted to elastically yield when assembled about the region of the nipple to constrict the proximal end of the sheath onto and about the nipple.

17. A catheter introducer as defined in claim 14 wherein the cap is formed to include an integral distal extension defining a strain relief about the sheath.

18. A catheter introducer as defined in claim 17 wherein the cap and strain relief extension are integrally molded from a flexible elastomeric material.

19. A catheter introducer as defined in claim 18 wherein the strain relief extension is of reduced cross-sectional dimension in a distal direction.

* * * * *

UNITED STATES PATENT AND TRADEMARK OFFICE
CERTIFICATE OF CORRECTION

PATENT NO. : 6,120,480
DATED : September 19, 2000
INVENTOR(S) : Zhang et al.

Page 1 of 1

It is certified that error appears in the above-identified patent and that said Letters Patent is hereby corrected as shown below:

Title page,
Under "Foreign Patent Documents" please insert: -- 0792660 09/1997 Europe -- and -- 9730746 08/1997 WIPO --.

Column 2,
Line 31, delete "for" and insert -- or -- therefor.
Line 54, after "adhesives," insert -- and --.
Line 55, after "Representative" insert -- examples --.

Column 7,
Line 16, delete "0.20", and insert -- 0.020 -- therefor.
Line 41, delete "at 61".

Column 10,
Line 45, delete "include" and insert -- includes -- therefor.

Column 12,
Line 28 (claim 1), delete "though" and insert -- through -- therefor.
Line 46 (claim 2), delete "though" and insert -- through -- therefor.

Column 13,
Line 39 (claim 10), delete "that" and insert -- than -- therefor.

Signed and Sealed this

Eleventh Day of September, 2001

*Attest:*

NICHOLAS P. GODICI
*Attesting Officer*     *Acting Director of the United States Patent and Trademark Office*